United States Patent
Luo et al.

(10) Patent No.: US 9,221,029 B2
(45) Date of Patent: Dec. 29, 2015

(54) AUTOMATIC SYSTEM FOR SYNTHESIZING $^{123}$I-MIBG AND AUTOMATIC DEVICE FOR SYNTHESIZING AND DISPENSING $^{123}$I-MIBG COMPRISING THE SAME

(71) Applicant: Institute of Nuclear Energy Research Atomic Energy Council, Executive Yuan, Taoyuan County (TW)

(72) Inventors: Tsai-Yueh Luo, Taoyuan County (TW); Te-Sheng Liang, Taoyuan County (TW); Ying-Hsia Shih, Taoyuan County (TW); Wuu-Jyh Lin, Taoyuan County (TW)

(73) Assignee: INSTITUTE OF NUCLEAR ENERGY RESEARCH ATOMIC ENERGY COUNCIL, EXECUTIVE YUAN, Longtan Township, Taoyuan County (TW)

( * ) Notice: Subject to any disclaimer, the term of this patent is extended or adjusted under 35 U.S.C. 154(b) by 2 days.

(21) Appl. No.: 14/464,461

(22) Filed: Aug. 20, 2014

(65) Prior Publication Data
US 2015/0056105 A1    Feb. 26, 2015

(30) Foreign Application Priority Data
Aug. 20, 2013    (TW) .................................. 102129819

(51) Int. Cl.
*B01J 19/24* (2006.01)
*B01J 19/00* (2006.01)
(Continued)

(52) U.S. Cl.
CPC .............. *B01J 19/0006* (2013.01); *A61K 51/04* (2013.01); *A61K 51/0406* (2013.01); *B01J 19/00* (2013.01);
(Continued)

(58) Field of Classification Search
CPC .......... B01J 19/00; B01J 19/24; A61K 51/04
USPC .................................. 422/159; 424/1.85, 1.37
See application file for complete search history.

(56) References Cited

U.S. PATENT DOCUMENTS 5,019,323 A * 5/1991 Lambrecht et al. ........... 376/201
6,773,686 B1 * 8/2004 Herscheid et al. ................ 423/2

FOREIGN PATENT DOCUMENTS

CN           201785324 U  *  4/2011

OTHER PUBLICATIONS

English translation of CN 201785324 U—Sep. 24, 2015.*
(Continued)

*Primary Examiner* — Walter D Griffin
*Assistant Examiner* — Huy-Tram Nguyen
(74) *Attorney, Agent, or Firm* — Muncy, Geissler, Olds & Lowe, P.C.

(57) ABSTRACT

The present invention relates to an automatic system for synthesizing iodine-123 meta-iodobenzylguanidine ($^{123}$I-MIBG), which comprises a first reactor for subjecting radioactive iodine-containing sodium iodide and meta-iodobenzylguanidine (MIBG) sulfate to an iodine-iodine exchange reaction to obtain radioactive iodine labeled MIBG; a purification unit for purifying the iodine labeled MIBG; and a second reactor for substituting a solvent used in purification with a phosphate buffer to obtain a phosphate solution containing $^{123}$I-MIBG. The present invention also relates to an automatic device for dispensing $^{123}$I-MIBG, which comprises the automatic system for synthesizing $^{123}$I-MIBG, a radioactivity measuring unit, and a dispensing and packing unit.

12 Claims, 2 Drawing Sheets

(51) Int. Cl.
*A61K 51/04* (2006.01)
*C07B 59/00* (2006.01)

(52) U.S. Cl.
CPC .............. *B01J 19/0013* (2013.01); *B01J 19/24* (2013.01); *C07B 59/00* (2013.01); *B01J 2219/00051* (2013.01); *B01J 2219/00182* (2013.01)

(56) References Cited

OTHER PUBLICATIONS

A. Quach et al. "Thyroid and Hepatic Function after High Dose $^{131}$I-Metaiodobenzylguanidine ($^{131}$I-MIBG) Therapy for Neuroblastoma" *Pediatric Blood Cancer*, Feb. 2011; 56(2): 191-201.

A. Flotats et al. "Proposal for standardization of $^{123}$I-metaiodobenzylguanidine (MIBG) cardiac sympathetic imaging by the EANM Cardiovascular Committee and the European Council of Nuclear Cardiology" *Eur. J. Nucl. Med. Mol. Imaging*, (2010) 37:1802-1812.

R. C. Kline et al., "Myocardial Imaging in Man with I-123 Meta-Iodobenzylguanidine" *J. Nucl. Med*, 22: 129-132, 1981.

D. Taïeb et al. "EANM 2012 guidelines for radionuclide imaging of phaeochromocytoma and paraganglioma" *Eur. J. Nucl. Med. Mol. Imaging*, (2012) 39: 1977-1995.

B. Kimmig et al. "Scintigraphy of a Neuroblastoma with I-131 Meta-Iodobenzylguanidine" *J. Nucl. Med.*, 25:773-775 1984.

* cited by examiner ated as $^{123}$I-MIBG hereinafter) and an automatic device for synthesizing and dispensing $^{123}$I-MIBG comprising the automatic system for synthesizing $^{123}$I-MIBG.

AUTOMATIC SYSTEM FOR SYNTHESIZING $^{123}$I-MIBG AND AUTOMATIC DEVICE FOR SYNTHESIZING AND DISPENSING $^{123}$I-MIBG COMPRISING THE SAME

CROSS-REFERENCE TO RELATED APPLICATION

Technical Field

The present invention relates to an automatic system for synthesizing iodine-123 meta-iodobenzylguanidine (abbreviated as $^{123}$I-MIBG hereinafter) and an automatic device for synthesizing and dispensing $^{123}$I-MIBG comprising the automatic system for synthesizing $^{123}$I-MIBG.

BACKGROUND

In the 1970s, Dr. Donald Wieland and his colleagues in the University of Michigan Medical School developed radioactive labeled meta-iodobenzylguanidine (MIBG) as a diagnostic contrast medium for adrenal medulla. The structure of the MIBG is similar to that of norepinephrine. It has been proved that tissues with normal sympathetic nerve distribution, such as hearts, salivary glands, and tumors that express neurohormone transporters, have high absorptivity for MIBG.

The first $^{131}$I-MIBG clinical report was published by the University of Michigan in 1980. The result shows that $^{123}$I-MIBG can be used for quantifying an expression level of amine in myocardial catecholamine. Since 1984, further studies have shown that high-dose $^{131}$I-MIBG can be further used for treating neuroblastoma. In 2012, the University of Michigan published The Report about the Therapy of $^{131}$I-MIBG, and the European Association of Nuclear Medicine (EANM) also published The Clinical Diagnosis Guideline for Pheochromocytoma in August, 2012, which is for the reference of clinical applications. At present, the radioactive iodine labeled MIBG has been widely applied to imaging diagnosis and treatment of neuroblastoma.

In recent years, the application of $^{123}$I-MIBG to the diagnosis of cardiac sympathetic functions gains more and more attention. $^{123}$I-MIBG myocardial scintigraphy has been proved valuable in diagnosing cardiomyopathy and heart failure, and especially in (1) predicting potential arrhythmia; (2) evaluating high-risk populations for heart failure; (3) improving knowledge about a reaction mechanism of elevated sympathetic activity in a heart failure. The $^{123}$I-MIBG can also be used for evaluating cardiac sympathetic functions of patients, so as to help choose suitable implantable cardioverter-defibrillators (ICDs). The Cardiovascular Committee of the EANM published Proposal for Standardization of $^{123}$I-metaiodobenzylguanidine (MIBG) Cardiac Sympathetic Imaging by the EANM Cardiovascular Committee and the European Council of Nuclear Cardiology in the European Journal of Nuclear Medicine and Molecular Imaging in 2010, and it is clear that the MIBG has a clinical application potential in cardiac sympathetic diagnosis.

Since its first clinical application report proposed by the University of Michigan in 1980, radioactive iodine labeled MIBG has been used clinically for 20 years. $^{131}$I and $^{123}$I-MIBG are radioisotopes of iodine. Although $^{123}$I-MIBG has the proper gamma ray (159 KeV), which makes it very suitable for imaging, its half-life period is only 13 hours. Therefore, the $^{123}$I-MIBG has to be produced by using middle-sized cyclotrons, which limits the transportation area thereof. I-131 labeled MIBG is mostly used for clinical diagnosis in foreign countries, and has been available on the market in Europe, America, Japan, and other countries. In 1994, The US Food and Drug Administration (FDA) also proved $^{131}$I-MIBG, which is called $^{131}$I intravenous agent (NDA 20-084), to be sold as a contrast medium for pheochromocytoma and neuroblastoma; in 2008, $^{123}$I-MIBG known as Iobenguane $^{123}$I-MIBG injection was also approved by the FDA (NDA 22-290) to be used as a tumor contrast medium (Adreview, GE Healthcare, Little Chalfont, UK), and in Europe, Japan, and other counties, it has been more than ten years since the $^{123}$I-MIBG and $^{131}$I-MIBG were allowed to go on sale.

The clinical application data of the MIBG is described as follows:

A. Imaging

In analysis and comparison of an MIBG imaging method and a fluorodeoxy-glucose-positron emission tomography (FDG-PET) method for neuroblastoma, imaging results of 21 neuroblastoma patients show that MIBG has higher sensitivity, especially at bones, while the FDG-PET has higher sensitivity at soft tissues. Therefore, the FDG-PET can compensate for the deficiency of MIBG. At present, computed tomography (CT) or magnetic resonance imaging (MRI) are the most commonly used for evaluating preliminary sites of tumors, and MIBG is applicable to imaging diagnosis after cancer metastasis.

During imaging using $^{123}$I, special attention should be paid to some factors that affects the imaging result, for example, drug interference, tumor periods, drug metabolism pathways, non-specificity of specific organs, and setting of imaging parameters. After false-positive and false-negative imaging results caused by specific factors are ruled out, $^{123}$I-MIBG is nearly 100% specifically bound to tumors, and is gathered in neuroblastoma cells after injection. Therefore, $^{123}$I-MIBG is a very useful tool for disease diagnosis, staging, and observation during treatment and prognosis.

B. Pharmacokinetics

After being injected intravenously, the MIBG is transmitted to neuroblast, and is mainly stored in cytoplasm of nerve cells. The MIBG is mainly excreted through the urinary system. One hour after the injection of the $^{131}$I-MIBG to neuroblastoma patients, 10% or lower of the $^{131}$I-MIBG still exists in the blood. 24 hours later, 57% of the $^{131}$I-MIBG is excreted out of the body through urine; and 48 hours later, 70% of the $^{131}$I-MIBG was excreted out of the body through urine. 90% of the MIBG is gathered in neuroblast, and the false-negative result is probably related to the change of the activity absorption mechanism caused by the differentiation of tumor cells or the drug interference.

The heart and salivary glands are controlled by sympathetic nerves, and the urinary tract and gastrointestinal system are MIBG excretion pathways. Therefore, these organs present very high MIBG expression. Intra-cavity non-specificity moves or decreases as the imaging time passes by, and can be easily distinguished during continuous image capturing.

C. Pharmacodynamics

The research report indicates that the treatment effective rate of $^{131}$I-MIBG on neuroblastoma is 30-40%. Most recent studies mainly focus on $^{131}$I-MIBG and chemotherapy and myeloablative stem cell transport combined therapies D. Safety and Side Effects The $^{131}$I-MIBG therapy has special side effects. The decrease degree of blood platelets and neutrophil leucocytes is associated with the therapy dosage absorbed by the body, because the specific absorption of megakaryocytes decreases bone marrow functions, especially when the $^{131}$I-MIBG therapy is performed after the chemotherapy. Despite the use of oral potassium iodide (KI), hypothyroidism still occurs.

Other side effects include nausea and vomiting, chest pain, fever, and impact on liver and kidney; some studies show that oral mucositis and sialoadenitis may also occur.

When $^{123}$I-MIBG is used for diagnosis, 92-100% of the patients have accumulated $^{123}$I-MIBG in salivary glands, because the salivary glands are controlled by sympathetic nerves. $^{131}$I-MIBG has a high clearance rate; in this study case, the saliva-to-plasma ratio is greater than 1.0 (ranging from 15 minutes to 48 hours), and most radioactivity is excreted through saliva in the form of free $^{131}$I ions, which not only leads to an error in imaging diagnosis but also increases the radiological dosage on oral mucosa.

Therefore, the radioactive labeled MIBG has been popularized in imaging diagnosis. However, the radioactive labeled MIBG is radioactive, and therefore during manufacturing, operators are threatened by radiation contamination. Therefore, it is urgent to provide a device capable of automatically synthesizing, dispensing, and measuring radioactivity of radioactive labeled MIBG.

SUMMARY

In view of the above, a main object of the present invention is to provide a system capable of automatically synthesizing $^{123}$I-MIBG, packing finished products of $^{123}$I-MIBG, and measuring radioactivity of $^{123}$I-MIBG, so as to reduce a radiation dosage received by operating personnel and produce high-quality nuclear medical diagnosis preparations that are applicable to diagnosing diseases such as pheochromocytoma, medullary thyroid carcinoma, paragangliomas, neuroblastoma, carcinoid tumor, cardiac sympathetic function, and myocardial infarction. The system of the present invention can be applied to routine production and supply of drugs, reduce radiation injury suffered by operating personnel and pollution of radioactive substances, and implement mass production for clinical use.

Chemical structures of MIBG and $^{123}$I MIBG are as follows:

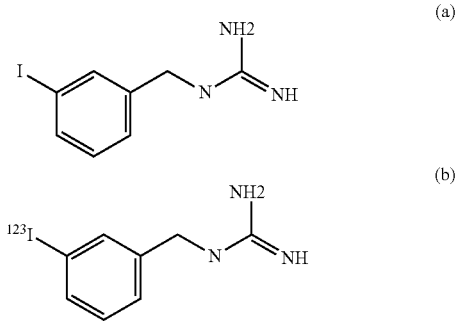

Accordingly, a first object of the present invention is to provide an automatic system for synthesizing $^{123}$I-MIBG, which comprises: a first reactor for subjecting radioactive iodine-containing sodium iodide (for example, rhenium-188, yttrium-90, and iodine-131) and meta-iodobenzylguanidine sulfate, which are fed into the first reactor through a line under the control of a solenoid valve, to an iodine-iodine exchange reaction to obtain radioactive labeled MIBG; and a purification unit for performing chemical separation and purification on the radioactive iodine labeled MIBG, which is fed into the first reactor through the line and under the control of the solenoid valve, by means of column chromatography with water and ethanol, to collect a fraction eluted with the ethanol; and a second reactor for distilling an ethanol eluent purified by the purification unit to remove the ethanol, and then a phosphate buffer is fed to obtain a phosphate buffered solution containing $^{123}$I-MIBG.

In the automatic system for synthesizing $^{123}$I-MIBG according to the present invention, the first reactor, the purification unit, and the second reactor are connected by lines; a reaction product may be transferred from the first reactor to the purification unit by using a solenoid valve in a pressurized gas pumping manner, a negative pressure suction manner, or a combination of the two manners, and transfer from the purification unit to the second reactor is controlled by a three-way valve. Moreover, the first reactor, purification unit, and second reactor can be disassembled from and assembled onto the automatic system for synthesizing $^{123}$I-MIBG according to the present invention, and the lines can be replaced.

In the automatic system for synthesizing $^{123}$I-MIBG, an ambient gas in the automatic synthesizing system is an inert gas, for example, nitrogen, helium, and neon; considering the availability and cost of the gas, nitrogen is preferable.

In the automatic system for synthesizing $^{123}$I-MIBG, the first reactor is further configured with a temperature controller for controlling a temperature of the iodine-iodine exchange reaction, and an activated carbon apparatus for absorbing unreacted free iodine, so as to prevent environmental pollution and radiation contamination on operating personnel during emission. When the reactants are fed into the first reactor, iodobenzylguanidine sulfate, ammonium sulfate and sodium acetate that function as reaction catalysts, and sodium iodide containing a radioactive iodine isotope are separately fed into the first reactor by using a solenoid valve and through a line, and an exchange reaction between $^{123}$I and iodine is performed at a temperature of 60 to 200° C., and preferably, at a temperature of 150 to 180° C.

Further, an additional automatic dispensing unit may be used to feed the reactants iodobenzylguanidine sulfate, ammonium sulfate, and sodium iodide containing a radioactive iodine isotope into the first reactor, and then the first reactor is placed into the automatic system for synthesizing $^{123}$I-MIBG according to the present invention, to start programs, such as feeding of sodium acetate and the like and heating, so as to perform the reaction. The above step of feeding the reactants into the first reactor may also be performed manually.

In the automatic system for synthesizing $^{123}$I-MIBG according to the present invention, one or more first reactors may be provided, for example, three or more, so as to perform a large quantity of reactions at the same time.

In the automatic system for synthesizing $^{123}$I-MIBG according to the present invention, the first reactor, purification unit, and second reactor are designed as a closed system, and processing steps therein are controlled by a computer program.

In the automatic system for synthesizing $^{123}$I-MIBG according to the present invention, the purification unit is a chromatography column, and preferably, is a reverse phase chromatography column such as an RP-18 column (for example: C-1, C12, C-8, and C-4). When the $^{123}$I-MIBG in the first reactor is transferred to the column by using a solenoid valve, ammonium sulfate, sodium acetate, and unreacted substances are first dissolved out by using water as an eluent, and discarded as liquid waste; then, the $^{123}$I MIBG is dissolved out by using ethanol as an eluent and collected in the second reactor. A three-way valve is connected following the purification unit, so as to control an eluate to be removed as liquid waste or collected in the second reactor.

In addition, the $^{123}$I-MIBG synthesized according to the present invention will be directly applied to human bodies while the solution obtained after the purification of the purification unit is an ethanol solution, which cannot be directly applied to human bodies, and therefore a step of removing the ethanol is required.

In the automatic system for synthesizing $^{123}$I-MIBG, the second reactor is also configured with a temperature controller, and in the second reactor, by means of heating controlled by the temperature controller, the ethanol is removed from the $^{123}$I-MIBG purified in the purification unit; a phosphate buffer is added in the second reactor also by using a solenoid valve, to formulate a phosphate buffered solution containing the $^{123}$I-MIBG, and the solution is filtered and sterilized by a filtering membrane, for example a 0.22 μm filtering membrane, and is collected in a collecting tank for later use or subsequent processing.

The $^{123}$I-MIBG synthesized according to the present invention will be directly injected to human bodies, and therefore the system operates in a sterile environment, and the phosphate buffer is a phosphate buffer suitable for injection to human bodies.

The second reactor may be equipped with an activated carbon apparatus for absorbing radioactive iodine vapor that is possibly released during heating and distillation and then discharging the liquid waste.

Before and after the synthesizing reaction, all the feed materials in the automatic system for synthesizing $^{123}$I-MIBG according to the present invention may be replaced with water to wash the lines by performing the process of each unit, and then all the feed materials are replaced with ethanol to clean the system by performing the process of each unit again. The operation of the automatic system for synthesizing $^{123}$I-MIBG according to the present invention may be controlled and driven automatically by using system control software on a computer.

A second object of the present invention is to provide an automatic device for synthesizing and dispensing $^{123}$I-MIBG, which comprises: the automatic system for synthesizing $^{123}$I-MIBG described above, for obtaining a phosphate buffered solution containing radioactive labeled MIBG; a radioactivity measuring unit, for measuring radioactivity of the radioactive labeled MIBG prepared in a synthesizing unit; and a dispensing and packing unit, for dispensing the $^{123}$I-MIBG with a required radioactivity dosage to each vial according to the radioactivity measured during the radioactivity measurement.

In the automatic device for synthesizing and dispensing $^{123}$I-MIBG, the automatic system for synthesizing $^{123}$I-MIBG is described above while the radioactivity measuring unit and the dispensing and packing unit are existing apparatuses, and therefore, no detailed description is provided. For example, the radioactivity measuring unit may be a Model CRC-25R radioactivity measuring unit purchased from CAPINTEC.INC., and the dispensing and packing unit may be a Model 402 dispensing and packing unit purchased from the GILSON company and a Model ADG-500 dispensing and packing unit purchased from Becquerel & Sievert Co., Ltd.

In the automatic device for synthesizing and dispensing $^{123}$I-MIBG according to the present invention, the dispensing and packing unit determines, according to an activity dosage (mCi) measured by the radioactivity measuring unit, the number of vials to which the $^{123}$I-MIBG is dispensed.

In the automatic device for synthesizing and dispensing $^{123}$I-MIBG, the dispensing and packing unit may further be configured with a clamp unit, which moves along x, y, and z axes in the synthesizing system to move the vial in which the $^{123}$I-MIBG is dispensed so that the vial is packed in a pig to obtain a finished pig product. The clamp unit may be a robotic arm.

The automatic device for synthesizing and dispensing $^{123}$I-MIBG according to the present invention may be controlled by a computer program on a computer.

DETAILED DESCRIPTION OF DISCLOSED EMBODIMENTS

The present invention will be described in detail in the following with reference to the accompanying drawings, which, however, are merely exemplary but not intended to limit the scope of the present invention.

Figure 1:
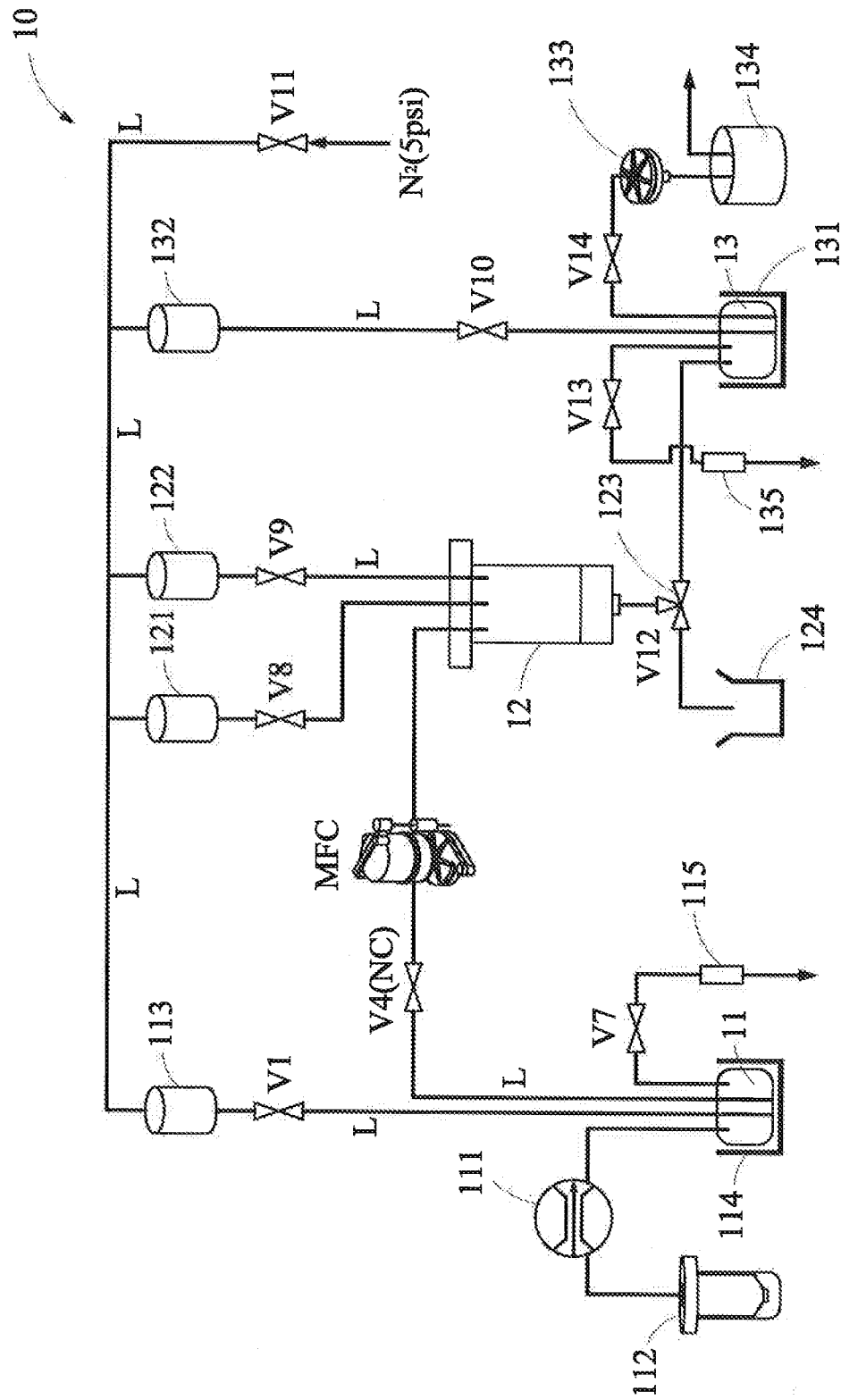
FIG. 1 is a configuration flow chart of an automatic system for synthesizing $^{123}$I-MIBG according to an implementation manner of the present invention.

First, referring to FIG. 1, FIG. 1 is a configuration flow chart of an automatic system for synthesizing $^{123}$I-MIBG according to an implementation manner of the present invention. As shown in FIG. 1, in an automatic system 10 for synthesizing $^{123}$I-MIBG according to the present invention, in a first reactor 11, radioactive iodine-containing sodium iodide, ammonium sulfate, and an MIBG sulfate solution are fed from a container 112 to the first reactor 11 under the control of a peristaltic pump 111 and through a line, and sodium acetate is fed from a container 113 to the first reactor 11 by using a solenoid valve V1 and through a line L, so as to perform an iodine-iodine exchange reaction, to obtain radioactive labeled MIBG. Then, the radioactive labeled MIBG is delivered to a next step, that is, a purification unit 12, by using a solenoid valve V4 and through a line L. Column chromatography is used, where the radioactive labeled MIBG delivered from the first reactor 11 is received, and then water is fed from a container 121 to the column by using a solenoid valve V8 and through a line L, to dissolve out the ammonium sulfate, sodium acetate, and unreacted substances, which are delivered as liquid waste to a liquid waste tank 124 through a three-way valve 123 and discarded. Subsequently, ethanol is fed from a container to the column 122 by using a solenoid valve V9, to perform elution so as to obtain an ethanol fraction solution containing $^{123}$I-MIBG, and the ethanol fraction solution is delivered to a second reactor 13 by using the three-way valve 123 and through a line L. In the second reactor 13, a temperature controller 131 is used to heat the ethanol fraction solution containing $^{123}$I-MIBG purified by the purification unit 12, to remove the solvent ethanol by means of distillation, and discharge the solvent ethanol by using a solenoid valve V13. Then, a phosphate buffer is fed from a container 132 to the second reactor 13 by using a solenoid valve V10 and through a line, to obtain a phosphate buffered solution containing $^{123}$I-MIBG.

In the automatic system for synthesizing $^{123}$I-MIBG, the first reactor 11, the purification unit 12, and the second reactor 13 are connected by lines L; the transfer of the reaction product from the first reactor 11 to the purification unit 12 is controlled by the solenoid valve V4, and the transfer from the purification unit 12 to the second reactor 13 is controlled by a three-way valve V12. Moreover, the first reactor 11, the purification unit 12, and the second reactor 13 are assembled on the automatic system for synthesizing $^{123}$I-MIBG according to the present invention in a removable manner.

An ambient gas in the automatic synthesizing system is an inert gas, for example, nitrogen, helium, and neon, and is preferably nitrogen. The ambient gas may be fed into the units by using a solenoid valve V11 and through lines L The first reactor 11 is further configured with a temperature controller 114 for controlling a temperature of the iodine-iodine exchange reaction; and an activated carbon apparatus 115 for absorbing unreacted free iodine that is released. In the first reactor 11, the exchange reaction between $^{123}$I and iodine is performed at a temperature of 60 to 200° C., and preferably, at a temperature of 150 to 180° C.

Moreover, the first reactor 11 can be assembled on and disassembled from the automatic synthesizing system freely, and therefore at the automatic dispensing unit, the reactant iodobenzylguanidine sulfate, ammonium sulfate, and sodium iodide containing a radioactive iodine isotope may be manually fed into the first reactor according to required amounts thereof, and then the first reactor is put into the automatic system for synthesizing $^{123}$I-MIBG according to the present invention, to start feeding sodium acetate and the like, heating, and other programs, so as to perform the reaction.

The first reactor 11, the purification unit 12, and the second reactor 13 are designed as a closed system, and the processing steps therein are controlled by a computer program; moreover, parameters set under the control of the computer can be changed as required, for example, an addition amount of the reactant can be changed according to the amount of product to be synthesized.

In the automatic system 10 for synthesizing $^{123}$I-MIBG according to the present invention, the purification unit 12 is a chromatography column such as an RP-18 column. When the $^{123}$I-MIBG obtained in the first reactor is transferred to the column by using the solenoid valve V4, water, which serves as an eluent, is first fed from the container 121 to the column 12 (namely, the purification unit) by using the solenoid valve V8, to dissolve out the ammonium sulfate, sodium acetate, and unreacted substances. With an outflow direction controlled by the three-way valve V12, the ammonium sulfate, sodium acetate, and unreacted substances are discharged to the liquid waste tank 124 as liquid waste and discarded. Then, the three-way valve V12 is switched to a direction to the second reactor 13, and ethanol, which serves as an eluent, is fed from the container 122 to the column 12 by using the solenoid valve V9, to dissolve out the $^{123}$I-MIBG, and the $^{123}$I-MIBG is collected in the second reactor 13.

Water for use in elution may be pure water, water for injection, distilled water, deionized water, and so on, and is preferably water for injection.

The second reactor 13 is also configured with a temperature controller 131, and in the second reactor 13, the $^{123}$I-MIBG purified in the purification unit 12 is heated by using the temperature controller 131, for example, the $^{123}$I-MIBG is heated to 50 to 200° C., and preferably, 70 to 100° C., to remove the ethanol. Then, the phosphate buffer is added from the container 132 to the second reactor 13 by using the solenoid valve V10, to formulate a phosphate buffered solution containing the $^{123}$I-MIBG, and by using a solenoid valve V14, the phosphate buffered solution is enabled to pass a filtering membrane 133, for example, a 0.22-μm filtering membrane, for filtration sterilization, and is collected in a collecting tank 134 for later use or further processing.

The second reactor 13 may further be equipped with an activated carbon apparatus 135, for absorbing radioactive iodine vapor that is possibly released during heating and distillation and discharging the liquid waste.

Before and after the reaction, the automatic synthesizing system needs to be cleaned. In this case, it is only necessary to replace the content in the container 113, container 121, container 122, and container 132 with water, and drive the process with an automatic cleaning function key in the computer program, thereby cleaning the lines, reactors, and units. Then, the content fed into the tank is replaced with ethanol, and the same process at each part is performed, thereby completing cleaning and sterilization.

Figure 2:
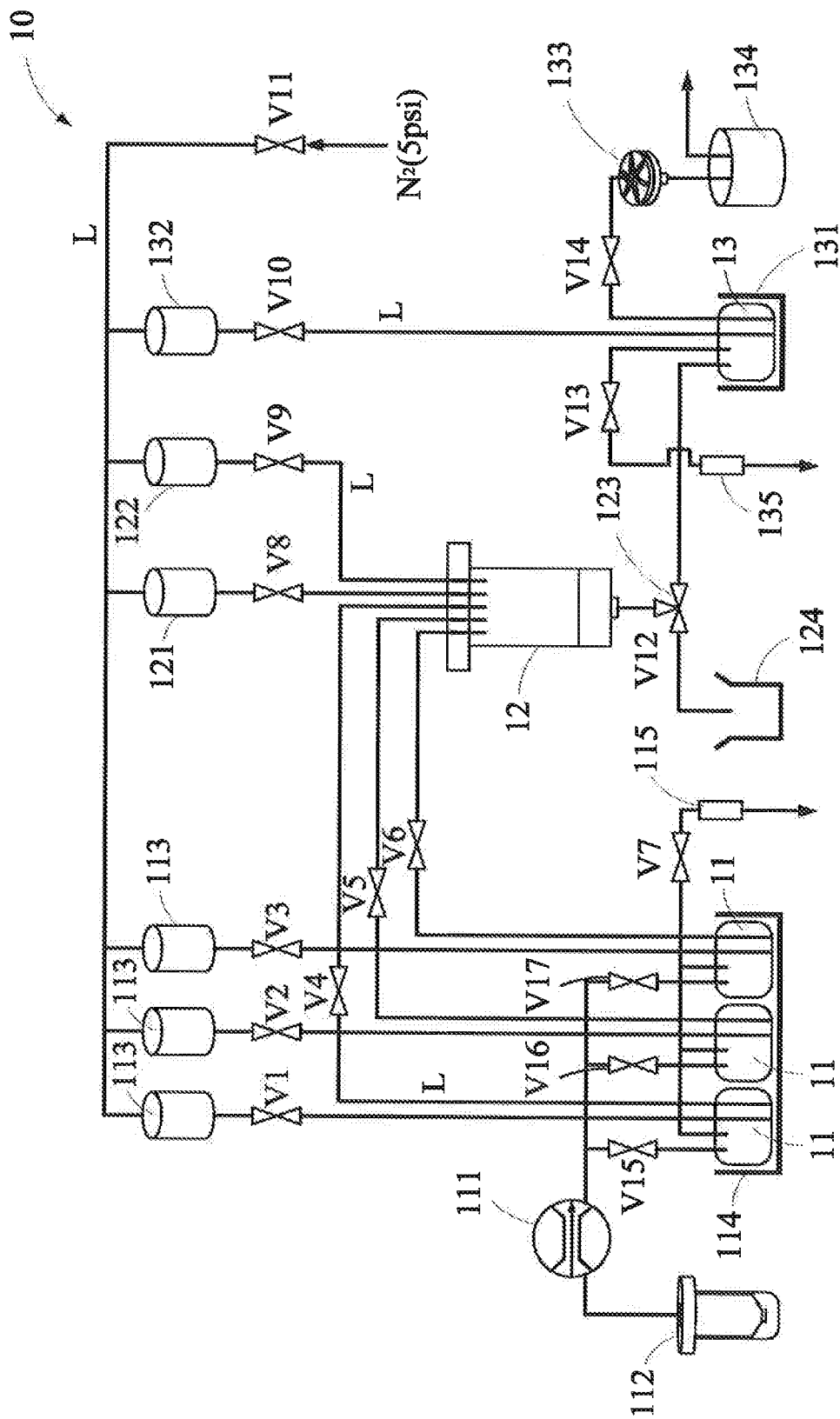
FIG. 2 is a configuration flow chart of an automatic system for synthesizing $^{123}$I-MIBG according to another implementation manner of the present invention.

Then, referring to FIG. 2, FIG. 2 is a configuration flow chart of an automatic system for synthesizing $^{123}$I-MIBG according to another implementation manner of the present invention. In FIG. 2, components the same as those in FIG. 1 are marked with the same signs and have the same functions as those in FIG. 1, and therefore, are not described repeatedly. The automatic system for synthesizing $^{123}$I-MIBG in FIG. 2 differs from the automatic system for synthesizing $^{123}$I-MIBG in FIG. 2 in that a plurality of first reactors 11 is configured in FIG. 2, to perform large-scale $^{123}$I-MIBG synthesizing.

The automatic system for synthesizing $^{123}$I-MIBG according to the present invention is controlled by a computer during the whole process, and therefore the dosage of each reactant, the reaction conditions, and so on can be controlled precisely; moreover, the reaction is performed in a closed loop environment, and therefore during the manufacturing process, the operator is not threatened by radiation contamination.

Moreover, an automatic device for synthesizing and dispensing $^{123}$I-MIBG according to the present invention includes: the automatic system for synthesizing $^{123}$I-MIBG shown in FIG. 1 or FIG. 2, for obtaining a phosphate buffered solution containing radioactive labeled MIBG; a radioactivity measuring unit, for measuring radioactivity of radioactive labeled MIBG sulfate prepared in the automatic synthesizing system; and a dispensing and packing unit, for dispensing the $^{123}$I-MIBG with a required radioactivity dosage to each vial according to the radioactivity measured during the radioactivity measurement, where the radioactivity measuring unit may be a Model CRC-25R radioactivity measuring unit purchased from CAPINTEC.INC., and the dispensing and packing unit may be a Model 402 dispensing and packing unit purchased from the GILSON company and a Model ADG-500 dispensing and packing unit purchased from Becquerel & Sievert Co., Ltd.

In the automatic device for synthesizing and dispensing $^{123}$I-MIBG, the dispensing and packing unit determines, according to an activity dosage (mCi) measured by the radioactivity measuring unit, the number of vials to which the $^{123}$I-MIBG is dispensed.

In the automatic device for synthesizing and dispensing $^{123}$I-MIBG, the dispensing and packing unit may further be configured with a clamp unit, which moves along x, y, and z axes in the synthesizing system to move the vial in which the $^{123}$I-MIBG is dispensed so that the vial is packed in a pig to obtain a finished pig product. The clamp unit may be a robotic arm.

The following describes the present invention in further details with an embodiment. The embodiment is merely a preferred implementation form of the present invention, which is an example for description but is not intended to limit the present invention. The scope of the present invention is defined by the scope of the appended patent claims.

Embodiment

By using the automatic synthesizing system 10 shown in FIG. 1, iodobenzylguanidine sulfate, ammonium sulfate, radioactive iodine-containing sodium iodide, and sodium acetate are fed into different reaction flasks, and the reaction flasks are assembled at feeding positions of the automatic synthesizing system, where lead shielding is required because the radioactive iodine-containing sodium iodide is radioactive. Then, with a female joint of an injection needle connected with a line joint, the injection needle pierces each sealed reaction flask, and the solenoid valve is controlled by a computer program so as to control a feed amount of each reactant.

In this embodiment, the reactant feed amounts are as follows: 0.3 mL of iodobenzylguanidine sulfate; 0.3 mL of ammonium sulfate; 0.54 mL (200-300 mCi) of radioactive iodine-containing sodium iodide; and 5 mL of sodium acetate.

Then, the computer is started to perform processes of the automatic synthesizing system shown in FIG. 1., and the reactants are fed into the first reactor 11 according to the amounts required; the reaction lasts 60 minutes with a reaction temperature controlled at 175° C. by the temperature controller 114, to perform $^{123}$I-iodine exchange of the iodobenzylguanidine sulfate, while unreacted sublimed iodine vapor is absorbed by the activated carbon apparatus 115 and the waste is discharged to the outside. After that, nitrogen is pressurized from a space above the first reactor, and the iodobenzylguanidine sulfate in which iodine is exchanged with $^{123}$I is delivered to the purification unit 12 by using the solenoid valve V4. Then water, which serves as an eluent, flows from the container 121 into the purification unit 12 by using the solenoid valve V8. At this time, the downstream three-way valve V12 of the purification unit 12 is switched to a direction to the liquid waste tank 124, and discharges an eluate after water elution to the liquid waste tank 124; then the three-way valve V12 is switched to a direction to the second reactor 13, and ethanol, which serves as an eluent, is fed from the container 122 into the purification unit 12 by using the solenoid valve V9; the ethanol effluent is collected in the second reactor 13, thereby obtaining an ethanol solution containing iodobenzylguanidine that has been subject to $^{123}$I-iodine exchange.

Then, the temperature controller 131 of the second reactor 13 is started to heat the second reactor 13 to 150° C., so as to evaporate the ethanol, and through the solenoid valve V13, the evaporated ethanol is filtered by the activated carbon apparatus 135 and discharged. Subsequently, the solenoid valve V10 is started to feed the phosphate buffer from the container 132 into the second reactor 13, to formulate a phosphate buffered solution containing the iodobenzylguanidine that has been subject to $^{123}$I-iodine exchange.

After that, by using the solenoid valve V14 and through the line L, the phosphate buffered solution containing the iodobenzylguanidine that has been subject to $^{123}$I-iodine exchange is filtered and sterilized by a 0.22-µm membrane filter 133, and is collected in the collecting tank 134. Then, the filtered and sterilized solution is delivered to a radioactivity measuring unit, which measures radioactivity of the radioactive labeled MIBG sulfate prepared by the synthesizing system, and then delivered to a dispensing and packing unit, which dispenses the $^{123}$I-MIBG with a required radioactivity dosage to each vial according to the radioactivity measured by the radioactivity measuring unit. At the same time, the dispensing and packing unit attaches on each a vial a label that indicates the radioactivity of the vial. Thus, the $^{123}$I MIBG is synthesized, dispensed, and packed.

In the foregoing processes, except the feeding of the reactants and installation of the elution reagent and phosphate buffer, all other processes are controlled by the computer. Therefore, the operators are not threatened by radioactive substances.

In addition, after the synthesizing, dispensing, packing, after a certain period of time or circulation, the reagents in the containers are replaced with water and ethanol and the foregoing processes are repeated to wash the automatic synthesizing system, so as to prepare for the next synthesizing program.

The present invention is described above with reference to the accompanying drawings and exemplary embodiments. However, the drawings and embodiments are merely used for describing the present invention rather than limiting the scope of the present invention. The scope of the present invention shall be limited by the scope of the patent claims of the present invention. Definitely, various changes and modifications made without departing from the spirit and scope of the patent claims of the present invention shall fall within the scope of the present invention.

What is claimed is:

1. An automatic system for synthesizing iodine-123 meta-iodobenzylguanidine ($^{123}$I-MIBG), comprising:
   a first reactor, for subjecting radioactive iodine-containing sodium iodide and meta-iodobenzylguanidine (MIBG) sulfate, which are fed into the first reactor through a line and under the control of a solenoid valve, to an iodine-iodine exchange reaction to obtain radioactive labeled MIBG;
   a purification unit, for performing elution purification on the radioactive iodine labeled MIBG, which is fed into the first reactor through the line by using the solenoid valve, by means of column chromatography with water and ethanol, to collect a fraction eluted with the ethanol; and a second reactor, for distilling an ethanol eluent purified by the purification unit to remove the ethanol, and then placing a phosphate buffer is fed to obtain a phosphate buffered solution containing $^{123}$I-MIBG.

2. The automatic system for synthesizing $^{123}$I-MIBG according to claim 1, wherein the first reactor, the purification unit, and the second reactor are connected by lines; a reaction product is transferred from the first reactor to the purification unit by using a solenoid valve in a pressurized gas pumping manner, and the transfer from the purification unit to the second reactor is controlled by a three-way valve.

3. The automatic system for synthesizing $^{123}$I-MIBG according to claim 1, wherein an ambient gas in the automatic synthesizing system is an inert gas.

4. The automatic system for synthesizing $^{123}$I-MIBG according to claim 1, wherein the first reactor is further configured with a temperature controller for controlling a temperature of the iodine-iodine exchange reaction; and an activated carbon apparatus for absorbing unreacted free iodine.

5. The automatic system for synthesizing $^{123}$I-MIBG according to claim 1, wherein one or more first reactors are provided.

6. The automatic system for synthesizing $^{123}$I-MIBG according to claim 1, wherein the purification unit is a chromatography column; water and ethanol are used as eluents in order, and the water eluate is discarded while the ethanol eluate is collected.

7. The automatic system for synthesizing $^{123}$I-MIBG according to claim 1, wherein the second reactor is also configured with a temperature controller and an activated carbon apparatus for absorbing ethanol that is removed by means of distillation through heating.

8. The automatic system for synthesizing $^{123}$I-MIBG according to claim 1, wherein the second reactor is further connected to a membrane filter, so as to sterilize and filter the phosphate buffered solution containing $^{123}$I-MIBG.

9. An automatic device for synthesizing and dispensing iodine-123 meta-iodobenzylguanidine ($^{123}$I-MIBG), comprising:

the automatic system for synthesizing $^{123}$I-MIBG according to claim 1, so as to obtain a phosphate buffered solution containing radioactive labeled meta-iodobenzylguanidine (MIBG);

a radioactivity measuring unit, for measuring radioactivity of the radioactive labeled MIBG prepared in a synthesizing unit; and a dispensing and packing unit, for dispensing the $^{123}$I-MIBG with a required radioactivity amount to each vial according to the radioactivity measured during the radioactivity measurement.

10. The automatic device for synthesizing and dispensing $^{123}$I-MIBG according to claim 9, wherein the dispensing and packing unit determines, according to an activity dosage (mCi) measured by the radioactivity measuring unit, the number of vials to which the $^{123}$I-MIBG is dispensed.

11. The automatic device for synthesizing and dispensing $^{123}$I-MIBG according to claim 10, wherein the dispensing and packing unit further comprises a clamp unit capable of moving along x, y, and z axes in the synthesizing system to move the vial in which the $^{123}$I-MIBG is dispensed so that the vial is packed in a pig to obtain a finished pig product.

12. The automatic device for synthesizing and dispensing $^{123}$I-MIBG according to claim 11, wherein the clamp unit is a robotic arm.

* * * * *